United States Patent [19]

Elbe et al.

[11] Patent Number: 4,870,092
[45] Date of Patent: Sep. 26, 1989

[54] 1,3-DIAZOLYL-2-PROPANOLS AS FUNGICIDAL AGENTS

[75] Inventors: Hans-Ludwig Elbe; Graham Holmwood; Erick Regel, all of Wuppertal; Karl H. Büchel, Burscheid; Paul Reinecke, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 578,246

[22] Filed: Feb. 8, 1984

[30] Foreign Application Priority Data

Mar. 2, 1983 [DE] Fed. Rep. of Germany ....... 3307216

[51] Int. Cl.[4] .................... A01N 43/64; A01N 43/50
[52] U.S. Cl. .................................... 514/383; 514/397
[58] Field of Search ................. 424/269; 514/383, 397

[56] References Cited

FOREIGN PATENT DOCUMENTS 0044605  1/1982  European Pat. Off. .
0061051  9/1982  European Pat. Off. .
0069442  1/1983  European Pat. Off. .

*Primary Examiner*—Douglas W. Robinson
*Assistant Examiner*—Joseph A. Lipovsky

*Attorney, Agent, or Firm*—Sprung Horn Kramer & Woods

[57] ABSTRACT

A fungicidal composition comprising a fungicidally effective amount of a 1,3-diazolyl-2-propanol of the formula

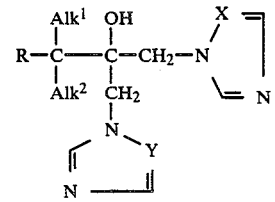

in which
Alk$^1$ is alkyl, and
Alk$^2$ is alkyl, or
Alk$^1$ and Alk$^2$ together complete a cycloaliphatic ring,
X is a nitrogen atom or the CH group,
Y is a nitrogen atom or the CH group, and
R is optionally substituted phenyl, phenylalkyl, phenoxy, phenylthio, phenoxyalkyl, phenylthioalkyl, benzyloxy or benzylthio, or a physiologically acceptable product thereof with an acid or metal salt in admixture with a diluent.

5 Claims, No Drawings

1,3-DIAZOLYL-2-PROPANOLS AS FUNGICIDAL AGENTS

The present invention relates to the use of new substituted 1,3-diazolyl-2-propanols as fungicidal agents.

It has already been disclosed that certain diazolyl derivatives, such as, for example, 2-(4-chlorophenyl)-1,3-di-(1,2,4-triazol-1-yl)-2-propanol, have fungicidal properties (compare EP-OS (European Published Specification) 0,044,605). However, the action of these compounds is not always completely satisfactory, especially when low amounts and concentrations are applied.

It has been found that the new substituted 1,3-diazolyl-2-propanols of the general formula

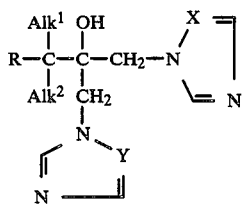

in which
Alk$^1$ represents straight-chain or branched alkyl, and
Alk$^2$ represents straight-chain or branched alkyl, or
Alk$^1$ and Alk$^2$ together complete a cycloaliphatic ring,
X represents a nitrogen atom or the CH group,
Y represents a nitrogen atom or the CH group and
R represents in each case optionally substituted phenyl, phenylalkyl, phenoxy, phenylthio, phenoxyalkyl, phenylthioalkyl, benzyloxy or benzylthio, and acid addition salts and metal salts complexes thereof, have good fungicidal properties.

Surprisingly, the substituted 1,3-diazolyl-2-propanols of the formula (I) to be used according to the invention display a better fungicidal activity than the diazolyl derivatives which are already known from the prior art, such as, for example, 2-(4-chlorophenyl)-1,3-di-(1,2,4-triazol-1-yl)-2-propanol, and which are closely related compounds structurally and from the point of view of their action. The use, according to the invention, of the new substances thus represents an enrichment of the art.

Formula (I) provides a general definition of the substituted 1,3-diazolyl-2-propanols to be used according to the invention. Preferably, in this formula,
Alk$^1$ represents straight-chain or branched alkyl with 1 to 4 carbon atoms; and
Alk$^2$ represents straight-chain or branched alkyl with 1 to 4 carbon atoms; or
Alk$_1$ and Alk$^2$ together complete a 3-membered to 7-membered cycloaliphatic ring,
X represents a nitrogen atom or the CH group;
Y represents a nitrogen atom or the CH group; and
R represents phenyl, phenylalkyl with 1 to 4 carbon atoms in the alkyl part, phenoxy, phenylthio, phenoxyalkyl with 1 to 4 carbon atoms in the alkyl part, phenylthioalkyl with 1 to 4 carbon atoms in the alkyl part, benzyloxy or benzylthio, each of which is optionally mono-, di- or tri-substituted in the phenyl part by identical or different substitutents, preferred substituents which may be mentioned being: halogen, alkyl with 1 to 4 carbon atoms, alkoxy and alkylthio with in each case 1 to 4 carbon atoms, halogenoalkyl, halogenoalkoxy and halogenoalkylthio with in each case 1 or 2 carbon atoms and 1 to 5 identical or different halogen atoms, such as, preferably, fluorine and chlorine atoms, nitro, cyano, hydroxyl, hydroxycarbonyl, alkoxycarbonyl with 1 to 4 carbon atoms in the alkyl part, hydroximinoalkyl with 1 to 4 carbon atoms in the alkyl part, alkoximinoalkyl with 1 to 4 carbon atoms in each alkyl part and phenyl, phenoxy, benzyl and benzyloxy, in each case optionally substituted by halogen and/or alkyl with 1 or 2 carbon atoms.

Particularly preferred compounds of the formula (I) are those in which
Alk$^1$ represents straight-chain or branched alkyl with 1 to 4 carbon atoms; and
Alk$^2$ represents straight-chain or branched alkyl with 1 to 4 carbon atoms; or
Alk$^1$ and Alk$^2$, together with the carbon atom to which they are bonded, represent cyclobutyl, cyclopentyl or cyclohexyl,
X represents a nitrogen atom or the CH group;
Y represents a nitrogen atom or the CH group; and
R represents phenyl, benzyl, phenethyl, phenoxy, phenylthio, phenyloxymethyl, phenoxyethyl, phenylthiomethyl, phenylthioethyl, benzyloxy or benzylthio, each of which is optionally mono- or di-substituted in the phenyl part by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro, cyano, hydroxy, hydroxycarbonyl, methoxycarbonyl, ehoxycarbonyl, hydroximinomethyl, 1-hydroximinoethyl, methoximinomethyl, 1-methoximinoethyl and phenyl, phenoxy, benzyl and benzyloxy, each of which is optionally substituted by fluorine, chlorine or methyl.

Very particularly preferred compounds of the formula (I) are those in which
Alk$^1$ represents methyl or ethyl; and
Alk$^2$ represents methyl or ethyl; or
Alk$^1$ and Alk$^2$, together with the carbon atom to which they are bonded, represent cyclobutyl, cyclopentyl or cyclohexyl,
X represents a nitrogen atom or the CH group;
Y represents a nitrogen atom or the CH group; and
R represents phenyl, benzyl, phenethyl, phenyloxymethyl, phenoxyethyl, phenylthiomethyl or phenylthioethyl, each of which is optionally mono- or di-substituted in the phenyl part by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro, cyano, hydroxy, hydroxycarbonyl, methoxycarbonyl, ethoxycarbonyl, hydroximinomethyl, 1-hydroximinoethyl, methoximinomethyl and 1-methoximinoethyl and phenyl, phenoxy, benzyl and benzyloxy, each of which is optionally substituted by fluorine, chlorine or methyl.

Very particularly preferred compounds of the formula (I) are also those in which
Alk$^1$ represents methyl or ethyl; and
Alk$^2$ represents methyl or ethyl; or Alk¹ and Alk², together with the carbon atom to which they are bonded, represent cyclobutyl, cyclopentyl or cyclohexyl, X represents a nitrogen atom or the CH group;

Y represents a nitrogen atom or the CH group; and

R represents phenoxy, phenylthio, benzyloxy or benzylthio, each of which is optionally mono- or disubstituted in the phenyl part by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro, cyano, hydroxyl, hydroxycarbonyl, methoxycarbonyl, ethoxycarbonyl, hydroximinomethyl, 1-hydroxyiminoethyl, methoximinomethyl and 1-methoximinoethyl and phenyl, phenoxy, benzyl and benzyloxy, each of which is optionally substituted by fluorine, chlorine or methyl.

Addition products of acids and those substituted 1,3-diazolyl-2-propanols of the formula (I) in which the substituents Alk¹, Alk², X, Y and R have the meanings which have already been mentioned as preferred for these substituents are also preferred compounds according to the invention.

Preferred acids which can be added on include the hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Addition products of salts of metals of main groups II. to IV. and of sub-groups I. and II. and IV. to VII. and those substituted 1,3-diazolyl-2-propanols of the formula (I) in which the substituents Alk¹, Alk², X, Y and R have the meanings which have already been mentioned as preferred for these substituents are also preferred compounds according to the invention.

The salts of copper, zinc, manganese, magnesium, tin, iron and nickel are particularly preferred here. Possible anions of these salts are those which are derived from acids leading to physiologically acceptable addition products. In this connection, particularly preferred acids of this type are the hydrogen halide acids, such as, for example, hydrochloric acid and hydrobromic acid, and nitric acid and sulphuric acid.

The active compounds to be used according to the invention are not yet known. However, they are the subject of Application Serial No., filed now pending, (German Patent Application P 33 07 721.7 [Le A 22 130] of the same application date), and they are obtained by reacting 2-azolylmethyl-oxiranes of the formula $$\begin{array}{c} Alk^1 \\ | \\ R-C-C-CH_2-N \\ | \quad / \backslash \\ Alk^2 \; CH_2-O \end{array} \begin{array}{c} X \\ / \\ \end{array} \begin{array}{c} \\ \\ N \end{array} \quad (II)$$

in which

Alk¹, Alk², R and X have the abovementioned meaning, with azoles of the formula $$H-N \begin{array}{c} Y \\ / \\ \\ N \end{array} \quad (III)$$

in which y has the abovementioned meaning,
in the presence of an inert organic diluent, such as, for example, alcohols, and if appropriate in the presence of a base, such as, for example, alkali metal alcoholates, at temperatures between 60° and 150° C.

Oxiranes of the formula (II) are known (compare U.S. Application Serial No. 352,689, filed 2/26/82, pending, they are the subject of earlier filed pending commonly assigned applications U.S. Ser. No. 458,086, filed 1/14/83 and U.S. Ser. No. 534,233, filed 9/21/83, both pending), and they can be obtained in a generally known manner, as also described in these applications, by a process in which azolyl-ketones of the formula $$\begin{array}{c} Alk^1 \\ | \\ R-C-CO-CH_2-N \\ | \\ Alk^2 \end{array} \begin{array}{c} X \\ / \\ \\ N \end{array} \quad (IV)$$

in which

Alk¹, Alk², R and X have the abovementioned meaning, either (a) are reacted with dimethyloxosulphoniummethylide of the formula $$\underset{(CH_3)_2SOCH_2}{\delta+\delta-} \quad (V)$$

in a manner which is known per se, in the presence of a diluent, such as, for example, dimethylsulphoxide, at temperatures between 20° C. and 80° C. (in this context, compare the statements in J. Am. Chem. Soc. 87, 1363-1364 (1965)), or (b) are reacted with trimethylsulphonium methyl-sulphate of the formula $$[(CH_3)_3S^\oplus]CH_3SO_4^\ominus \quad (VI)$$

in a manner which is know per se, in the presence of an inert organic solvent, such as, for example, acetonitrile, and in the presence of a base, such as, for example, sodium methylate, at temperatures between 0° C. and 60° C., preferably at room temperature (compare also the statements in Heterocycles 8, 397 (1977)).

If appropriate, the oxiranes of the formula (II) thus obtained can be further reacted directly, without being isolated.

The azolyl-ketones of the formula (IV) are known (compare U.S. application Ser. No. 481,615, filed 4/4/83, now pending, and U.S. Application 352,689, supra, where they can be prepared by processes which are known in principle).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The metal salt complexes of compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Cochliobolus species, such as *Cochliobolus sativus;* Botrytis species, such as against the causative organism of grey mould on strawberries and grapes (*Botrytis cinerea*); and furthermore also for combating powdery mildew, rust, Septoria, Cercosporella and *Pyrenophora teres* on cereal and against Venturia species in fruit growing, as well as rice diseases, such as *Pyricularia oryzae* and *Pellicularia sasakii.*

The compounds according to the invention also exhibit a good in vitro fungicidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds which extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis productions; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.2% by weight, are required at the place of action.

PREPARATION EXAMPLES

Example 1

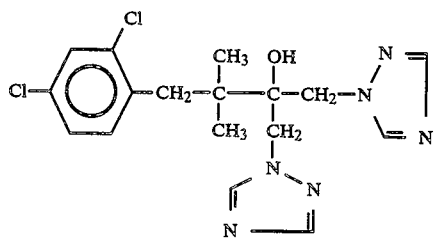

3.7 g (52.6 mmol) of 1,2,4-triazole are added to a solution of 0.11 g (47 mmol) of sodium in 30 ml of n-propanol at room temperature, while stirring. The mixture is heated to the reflux temperature and a solution of 15.4 g (47 mmol) of 2-(2,4-dichlorophenyl-tert.-butyl)-2-(1,2,4-triazol-1-yl-methyl)-oxirane in 20 ml of n-propanol is added. The reaction mixture is heated under reflux for 15 hours and then cooled and poured onto water. It is extracted with methylene chloride and the organic phase is dried over sodium sulphate and concentrated. The residue is purified by column chromatography (silica gel; ethyl acetate:cyclohexane=3:1). 3.5 g (18.8% of theory) of 4-(2,4-dichlorophenyl)-3,3-dimethyl-2-(1,2,4-triazol-1-yl-methyl)-1-(1,2,4-triazol-1-yl)-2-butanol of melting point 126° C. are obtained.

Preparation of the starting substance

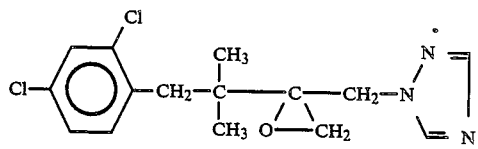

15.7 g (71.2 mmol) of trimethyl sulphoxonium iodide are dissolved in 16 g of dimethylsulphoxide, under a nitrogen atmosphere. 9.4 g (71.2 mmol) of potassium tert.-butylate is added at room temperature, while cooling. The mixture is subsequently stirred for 6 hours and a solution of 20 g (64.1 mmol) of (4-2,4-dichlorophenyl)-3,3-dimethyl-1-(1,2,4-triazol-1-yl)-2-butanone in 30 ml of tetrahydrofuran is then added. The reaction mixture is stirred at room temperature for 15 hours and under reflux for 4 hours, cooled and poured onto water. It is extracted with methylene chloride and the organic phase is dried over sodium sulphate and concentrated in vacuo. 15.4 g (73.7% of theory) of 2-(2,4-dichlorophenyl-tert.-butyl)-2-(1,2,4-triazol-1-yl-methyl)-oxirane of refractive index n$_D^{20}$=1.5539 are obtained.

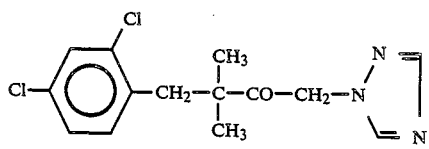

30 g (0.09 mol) of 1-bromo-4-(2,4-dichlorophenyl)-3,3-dimethyl-2-butanone, 12.4 g (0.18 mol) of 1,2,4-triazole and 24.8 g (0.18 mol) of potassium carbonate are heated under reflux in 300 ml of acetone for 6 hours. The mixture is then allowed to cool and is filtered with suction and the mother liquor is concentrated in vacuo. The residue is taken up in methylene chloride and the mixture is washed with water, dried over sodium sulphate and concentrated in vacuo. The residue is recrystallized from diethyl ether. 12.8 g (45.6% of theory of 4-(2,4-dichlorophenyl)-3,3-dimethyl-1-(1,2,4-triazol-1-yl)-2-butanone of melting point 85° C. are obtained.

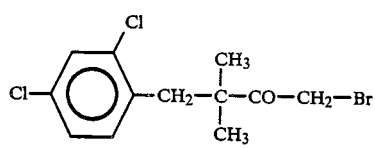

13.4 ml (0.26 mol) of bromine are slowly added dropwise to a solution of 64.5 g (0.26 mol) of 4-(2,4-dichlorophenyl)-3,3-dimethyl-2-butanone in 600 ml of chloroform at room temperature. The reaction solution is subsequently stirred at room temperature for 1 hour. It is then concentrated by distilling off the solvent. 84.3 g (100% of theory) of crude 1-bromo-4-(2,4-dichlorophenyl)-3,3-dimethyl-2-butanone are obtained as an oil, which is further reacted directly.

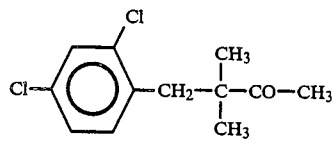

172 g (2 moles) of methyl isopropyl ketone, 391 g (2 moles) of 2,4-dichlorobenzyl chloride, 20 g of tetrabutylammonium bromide and 140 g (2.5 moles) of powdered potassium hydroxide are heated under reflux for 15 hours. The mixture is allowed to cool and water is added. The organic phase is separated off, dried over sodium sulphate and subjected to fractional distillation. 129 g (26.4% of theory of boiling point 90°–95° C./0.05 mbar are obtained.

The following compounds of the general formula

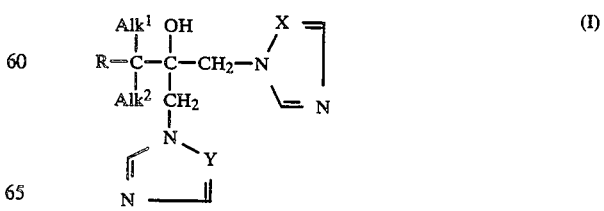

are obtained in a corresponding manner:

| Example No. | R | Alk¹ | Alk² | X | Y | Melting point [°C.] Refractive index [$n_D^{20}$]; |
|---|---|---|---|---|---|---|
| 2 | 4-Cl-C₆H₄-CH₂- | CH₃ | CH₃ | N | N | 132 |
| 3 | 4-CH₃-C₆H₄-CH₂- | CH₃ | CH₃ | N | N | 124 |
| 4 | 4-Cl-C₆H₄-O-CH₂- | CH₃ | CH₃ | N | N | 110–29 |
| 5 | 4-Cl-C₆H₄-S-CH₂- | CH₃ | CH₃ | N | N | 124 |
| 6 | 4-Cl-C₆H₄-O- | CH₃ | CH₃ | N | N | 128 |
| 7 | 4-Cl-C₆H₄-O-CH₂CH₂- | CH₃ | CH₃ | N | N | 1.5460 |
| 8 | 4-Cl-C₆H₄-CH₂- | CH₃ | CH₃ | CH | N | 220(× HCl) |
| 9 | 4-Cl-C₆H₄-O-CH₂CH₂- | CH₃ | CH₃ | CH | N | 1.5478 |
| 10 | 4-F-C₆H₄-CH₂- | CH₃ | CH₃ | N | N | 129 |
| 11 | 4-Cl-C₆H₄- | —CH₂—CH₂—CH₂— | | N | N | 78 |
| 12 | 4-Cl-C₆H₄- | CH₃ | CH₃ | N | N | 48 |
| 13 | 3,4-Cl₂-C₆H₃- | CH₃ | CH₃ | N | N | 138 |

-continued

| Example No. | R | Alk¹ | Alk² | X | Y | Melting point [°C.] Refractive index [$n_D^{20}$]; |
|---|---|---|---|---|---|---|
| 14 | Cl, F-phenyl-CH₂— | CH₃ | CH₃ | N | N | 147 |
| 15 | Br, F-phenyl-CH₂— | CH₃ | CH₃ | N | N | 144 |

USE EXAMPLES

The compound shown below is used as the comparison substance in the examples which follow:

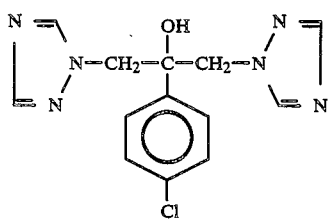
(A)

EXAMPLE A

*Cochliobolus sativus* test (barley)/protective

Solvent: 100 parts by weight of dimethylformamide.
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaulation is carried out 7 days after the inoculation.

In this test, a clearly superior activity compared with the prior art is shown, for example, by the compounds according to the following preparation examples: 2, 3, 1 and 5, as can be seen in Table A.

TABLE A

*Cochliobolus sativus* test (barley)/protective

| Active compound | Active compound concentration in the spray liquor in % by weight | Disease infestation in % of the untreated control |
|---|---|---|
| (A) (known) [structure with Cl] | 0.025 | 100 |
| (2) [structure with CH₂-phenyl-Cl] | 0.025 | 0.0 |

TABLE A-continued

Cochliobolus sativus test (barley)/protective

| Active compound | Active compound concentration in the spray liquor in % by weight | Disease infestation in % of the untreated control |
|---|---|---|
| (3) Compound with triazole groups, quaternary C with CH₃ and CH₂-C₆H₄-CH₃ substituents | 0.025 | 12.5 |
| (1) Compound with triazole groups, quaternary C with CH₃ and CH₂-C₆H₃Cl₂ substituents | 0.025 | 0.0 |
| (5) Compound with triazole groups, quaternary C with CH₃ and CH₂-S-C₆H₄-Cl substituents | 0.025 | 21.2 |

EXAMPLE B

Botrytis test (beans)/protective

Solvent: 4.7 parts by weight of acetone.

Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the following preparation examples: 2, 3 and 7, as can be seen in Table B.

TABLE B

Botrytis test (beans)/protective

| Active compound | Infestation in % at an active compound concentration of 250 ppm |
|---|---|
| (A) (known) — Compound with triazole groups and p-Cl phenyl | 100 |

TABLE B-continued

Botrytis test (beans)/protective

| Active compound | Infestation in % at an active compound concentration of 250 ppm |
|---|---|
| (2) [structure: triazolyl compound with CH2-C(OH)-CH2-N linkages, H3C-C=CH3, CH2-phenyl-Cl] | 75 |
| (3) [structure: triazolyl compound with CH2-C(OH)-CH2-N linkages, CH3-C-CH3, CH2-phenyl-CH3] | 26 |
| (7) [structure: triazolyl compound with CH2-C(OH)-CH2-N linkages, CH3-C-CH3, CH2CH2-O-phenyl-Cl] | 0 |

It will be appreciated that the instant specification and examples are set forth by way of illustration and not limitation, and that various modifications and changes may be made without departing from the spirit and scope of the present invention.

We claim:

1. A method of combating fungi which comprises administering to such fungi or to a fungus habitat a fungicidally effective amount of a 1,3-diazolyl-2-propanol of the formula

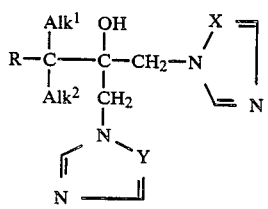

in which
- Alk$^1$ is methyl, and
- Alk$^2$ is methyl, or
- Alk$^1$ and Alk$^2$ together complete a cyclobutyl ring,
- X is a nitrogen atom or the CH group,
- Y is a nitrogen atom or the CH group, and
- R is phenyl, which is optionally mono- or di-substituted by chlorine, or is benzyl, which is optionally mono- or di-substituted in the phenyl part by fluorine, chlorine, bromine, methyl, trifluoromethoxy and/or trifluoromethylthio, or is phenoxy, which is optionally mono- or di-substituted by chlorine, or is phenoxymethyl or phenoxyethyl, each of which is optionally mono- or di-substituted in the phenoxy part by chlorine, or is phenylthiomethyl, which is optionally mono- or di-substituted in the phenyl part by chlorine, or a physiologically acceptable product thereof with an acid or metal salt in admixture with a diluent.

2. The method according to claim 1, wherein the active compound is 4-(2,4-dichlorophenyl)-3,3-dimethyl-2-(1,2,4-triazol-1-yl-methyl)-1-(1,2,4-triazol-1-yl-2-butanol of the formula

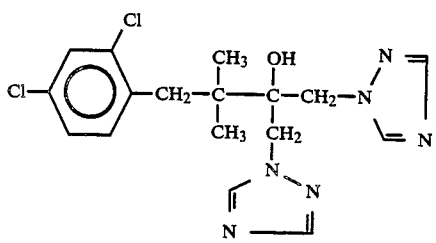

or a physiologically acceptable product thereof with an acid or metal salt in the admixture with a diluent.

3. The method according to claim 1, wherein the active compound is 4-(4-chlorophenyl)-3,3-dimethyl-2-(1,2,4-triazol-1-yl-methyl)-1-(1,2,4-triazol-1-yl)-2-butanol of the formula

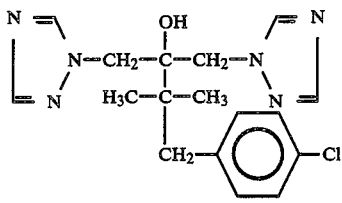

or a physiologically acceptable product thereof with an acid or metal salt in the admixture with a diluent.

4. The method according to claim 1, wherein the active compound is 4-(4-methylphenyl)-3,3-dimethyl-2-(1,2,4-triazol-1-yl-methyl)-1-(1,2,4-triazol-1-yl)-2-butanol of the formula

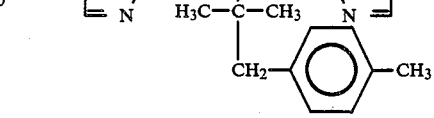

or a physiologically acceptable product thereof with an acid or metal salt in the admixture with a diluent.

5. The method according to claim 1, wherein the active compound is 5-(4-chlorophenoxy)-3,3-dimethyl-2-(1,2,4-triazol-1-yl-methyl)-1-(1,2,4-triazol-1-yl)-2-pentanol of the formula

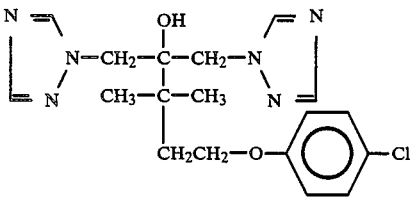

or a physiologically acceptable product thereof with an acid or metal salt in the admixture with a diluent.

* * * * *